United States Patent [19]

Detty

[11] 4,323,058
[45] Apr. 6, 1982

[54] ANKLE BRACE

[76] Inventor: Garnett E. Detty, 525 General Muhlenberg Rd., King of Prussia, Pa. 19406

[21] Appl. No.: 196,224

[22] Filed: Oct. 14, 1980

[51] Int. Cl.³ .............................................. A61F 3/00
[52] U.S. Cl. .................................. 128/80 H; 128/166
[58] Field of Search ...................... 128/80 H, 165, 166

[56] References Cited

U.S. PATENT DOCUMENTS

| | | | |
|---|---|---|---|
| 1,040,279 | 10/1912 | Collis | 128/166 |
| 1,231,332 | 6/1917 | Collis | 128/166 |
| 1,374,669 | 4/1921 | McClellan | 128/166 |
| 3,073,305 | 1/1963 | Biggs, Jr. et al. | 128/80 H X |
| 3,674,023 | 7/1972 | Mann | 128/166 |

*Primary Examiner*—John D. Yasko
*Attorney, Agent, or Firm*—Caesar, Rivise, Bernstein & Cohen, Ltd.

[57] ABSTRACT

An ankle brace comprising a jacket having a lateral side portion on which a pair of arcuate members are pivotably secured for conformance about the underlying malleolus. The jacket is arranged to be laced about the ankle by a first lace and with the arcuate members being secured together by a second lace to enable the members to closely conform and surround each malleolus to provide bracing and support thereto. A lift strap is secured to the lateral side of the jacket adjacent the bottom edge thereof and is arranged to be wrapped around the jacket in a figure-eight pattern for securement to the medial side. The strap is formed of an elastic material to closely conform to the jacket and to provide an upward lifting force to the jacket.

20 Claims, 6 Drawing Figures

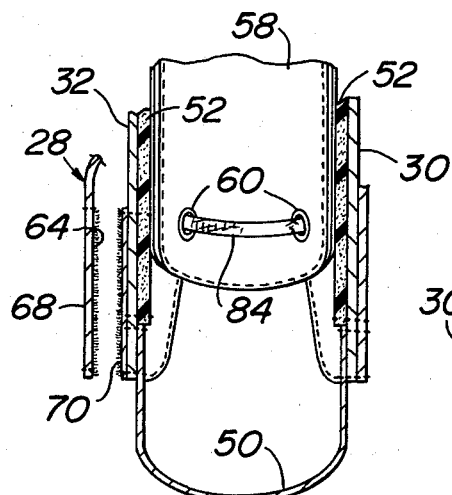
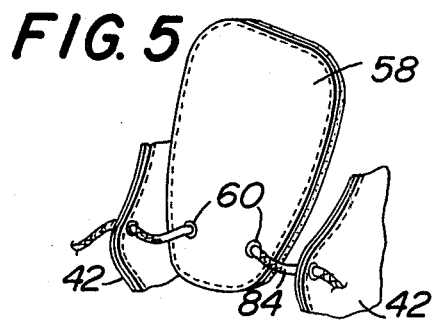
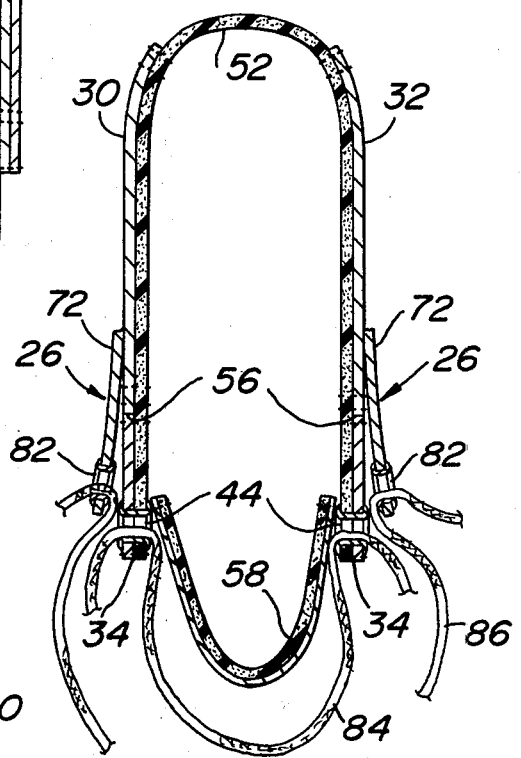
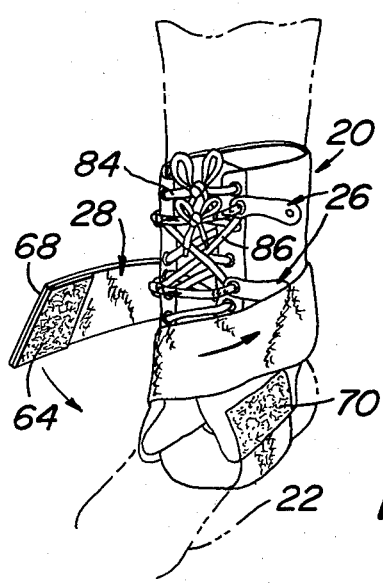

ANKLE BRACE

This invention relates generally to orthopedic devices and more particularly to ankle braces and supports.

Various ankle supports and braces have been disclosed in the patent literature and are commercially available as an alternative to conventional taping for providing restorative bracking and support for an injured or weakened ankle or for protecting a healthy ankle from injury.

For example, in U.S. Pat. No. 3,970,083 (Carrigan), there is disclosed an ankle support including a pliable single-piece jacket which is fittable about a person's foot and ankle. Elongated stiffening strips are joined to opposite sides of the jacket and define generally inverted T-shaped stiffened regions on the sides of the jacket. The jacket includes lacing means for tightening it about the ankle and foot and a tongue which is held in place by the lacing means. The stiffening strips form a plurality elongated stiffening regions which, when the jacket is fitted on the ankle extend generally parallel to the natural ligaments in the ankle, with the point of intersection extending over the lateral malleolus in the ankle.

In U.S. Pat. No. 4,085,746 (Castiglia), there is disclosed an ankle strap in the form of an elongated panel having first fastening means secured to a first elongated end portion of the panel and second fastening means spaced therefrom. The second fastening means is wrapped around the arch portion of a foot. The portion of the panel between the two fastening means is inelastic. Third fastening means is disposed at the other elongated end portion of the elastic panel for releasable securably fastening the panel about the ankle and arch portion after the panel has been alternately wrapped about the ankle and arch portion in a predetermined manner.

In U.S. Pat. No. 3,028,361 (Shapiro), there is disclosed an ankle support in the form of a jacket comprising substantially coextensive inner and outer plys of leather strips shaped to surround the ankle and underly the instep. Elastic ribbing is provided between the leather strips. The front of the jacket includes lacing means and a strap atttached to one side of the jacket adjacent the front for extension across the front edges and for releasable securement to the other side of the jacket.

Various ankle supports are commercially available. For example, Kramer Products, Inc. of Gardner, Kan. offers a support sold under the designation "Ankle Stabilizer No. 70". That support comprises a lacable jacket arranged to receive the ankle and foot of the wearer and includes a pair of inelastic straps arranged to be wrapped and releasably secured about the ankle to form a generally figure-eight stabilizing strap.

As is known, in the ankle there are a large number of ligamental and muscle attachments. In a chronic sprained ankle such attachments may be very weak and substantial support in that area is of considerable importance. Such support must be accomplished without sacrificing ankle mobility.

It has been found that prior art ankle braces which are designed to permit relative free motion of the ankle do not provide sufficient support for the muscles and ligaments to prevent overstressing or damage. In particular, prior art devices have exhibited a tendency to allow the foot to roll inward.

It is a general object of the instant invention to provide an ankle brace which overcomes the disadvantages of the prior art.

It is a further object of the instant invention to provide an ankle brace which includes means for improving the quality of mechanical fixation of the brace to the ankle to support the joint capsule and ligamentis attachments.

It is still a further object of the invention to provide an ankle brace which enables the close application of a constraining force to the ankle to improve stability below the malleoli to thereby control overinversion-eversion motion of the ankle.

It is still a further object of the instant invention to provide an ankle support which enables the close application of a localized constraining force to a tramatized ankle joint to facilitate the proprioceptive return thereof.

These and other objects of the instant invention are achieved by providing an ankle brace for securement on the ankle and contiguous foot and leg portions of a person. The ankle brace comprises a jacket, malleoli stabilization means and lift strap means. The jacket includes a medial side portion and a lateral side portion, each having a bottom, top, front and rear edge, with elastic means connecting said portions together at their rear edges and at their bottom edges. The front edges of both side portions are arranged to be secured together by laces so that the jacket fits about the ankle and contiguous portions of the foot and leg of the wearer, with the medial side portion of the jacket located over the medial side of the ankle and with the lateral side portion of the jacket located over the lateral side of the ankle. The malleoli stabilizing means comprise lateral stabilizing means secured to the lateral side portion of said jacket for surrounding the external or lateral malleolus and medial stabilizing means secured to the medial side portion of said jacet for surrounding the internal or medial malleolus. The lateral and medial stabilizing means are arranged to be releasably secured together by a lace. The lift strap means is an elongated member having a pair of ends, each arranged for securement to a respective side portion of said jacket, with the intermediate portion of the strap being wrapped about the instep and the ankle to provide an upward lifting force to the jacket.

Other objects and may of the attendant advantages of the instant invention will be readily appreciated as the same becomes better understood by reference to the following detailed description when considered in connection with the accompanying drawing wherein:

FIG. 3 is a sectional view taken along line 3—3 of FIG. 2;

FIG. 4 is an enlarged sectional view taken along line 4—4 of FIG. 2;

FIG. 5 is a reduced perspective view of a portion of the ankle brace; and

FIG. 6 is a reduced perspective view showing the application of the ankle brace on a person's ankle.

Turning now to the various figures of the drawing wherein like reference characters refer to like parts, there is shown at 20 an ankle brace in accordance with the instant invention.

Figures 1, 2:
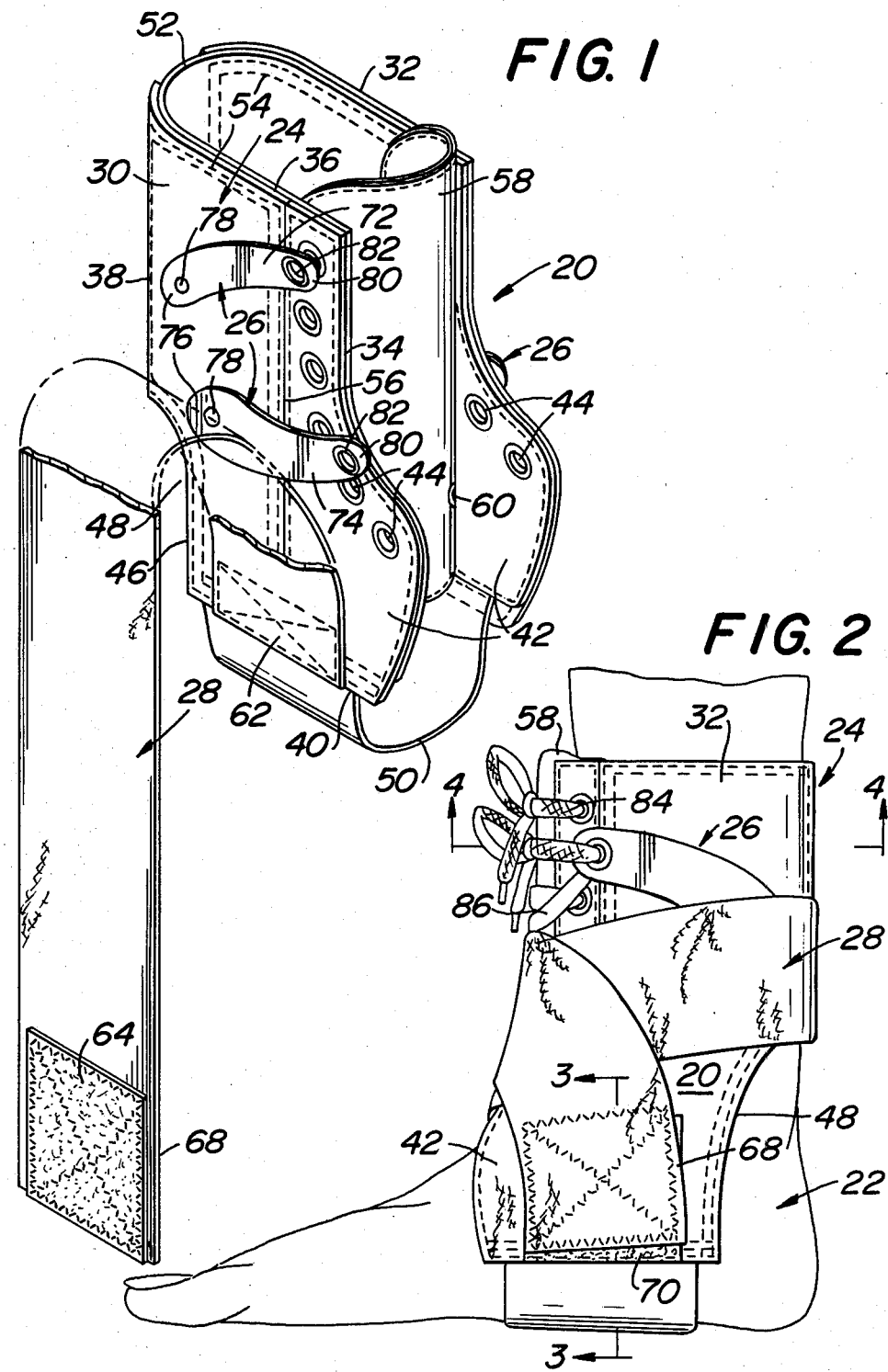
FIG. 1 is a perspective view of the ankle brace of the invention.
FIG. 2 is a side elevational view of the ankle brace disposed on a person's ankle.

The brace 20 is arranged to be worn on the ankle 22 to provide support while permitting relatively free motion. To that end as shown in FIG. 2, the brace 20 basically comprises a jacket 24, malleoli stabilization means 26 and lift means 28. The jacket 24 is shown clearly in FIGS. 1, 3 and 4 and basicly comprises a lateral side portion 30 and a medial side portion 32 and is preferably formed of a flexible material, such as, foam backed vinyl. Each side portion includes a front edge 34, a top edge 36, a rear edge 38 and a lower edge 40. The front edge 34 of each portion projects forward adjacent the lower edge 40 to form a stirrup portion 42. A plurality of eyelets 44 extend down each side portion along the front edge 34 from the top edge to approximately the forward-most point on the stirrup portion.

The back edge 38 is cut away by an arcuate recess 46 contiguous with the lower edge to form a heel-receiving space 48.

The lower edges 40 of the respective side portions 30 and 32 are connected together by a flexible, elastic strap 50 secured to each side portion by stitch lines. The back edge 38 of the side portions are connected together by a flexible, elastic web 52. The web 52 forms a lining for the jacket 24 and is preferably formed of an elastic material which provides good thermal insulation, such as neoprene foam. The liner 52 is secured to the side portion 30 and 32 by stitch lines 54 extending about the periphery of the side portions.

Each side portion 30 and 32 includes a flexible joint 56 (FIG. 1) extending vertically from the top to the bottom edge. The joint 56 is in the form of a slit extending fully through the material forming the side portion but not the liner. The liner is secured to the side portions contiguous with the joint 56 by the stitch lines 54. The joint 56 enables the side portions to flex readily to more closely conform with the wearer's ankle when the jacket 24 is laced, as will be described later.

The jacket 24 includes a separate or floating tongue 58, which is shown clearly in FIG. 5. The tongue 58 is of conventional shape and includes a pair of eyelets 60 adjacent its lower end for receipt of a lace to secure the tongue to the jacket.

The lift means 28 comprises a flexible, elastic strap having a first end 62 which is fixedly secured, as by stitch lines, to the lateral side portion 30 adjacent the lower edge 40. Releasable securement means 64 is located at the opposite end 68 of the strap. The lift strap is arranged to be wrapped in a figure-eight pattern around the jacket, after the jacket has been laced on, as shown in FIG. 6, so that the releasable securement means 64 secures the strap end 68 to the medial side portion 32.

In accordance with the preferred embodiment of this invention, the releasable fastening means 64 comprises one component of a hook and loop fastening system, such as sold under the trademark VELCRO by Velcro Manufacturing Company of Manchester, N. H., with the means 64 being the hook component. The other component of the fastening system, namely, the loop component 70, is fixedly secured to the outer surface of the medial side portion 32 contiguous with the lower edge 40 thereof.

Referring now to FIGS. 1, 2 and 4, it can be seen that the malleoli stabilizing means comprise two pairs of arcuate members, one pair being secured to the lateral side portion of the jacket, and hence being referred to as the lateral stabilizing means, and the other pair of arcuate portions being secured to the medial side portion, and being referred to as the medial stabilizing means. The lateral and medial stabilizing means are of identical construction and hence only the lateral stabilizing means will be described in detail hereinafter.

As can be seen, the lateral stabilizing means comprises an upper arcuate member 72 and a lower arcuate member 74. The members 72 and 74 are preferably performed of a flexible material, such as leather. Each arcuate member includes a first end 76 which is pivotably connected, via a rivet 78, to the lateral side portion of the jacket. Accordingly, each arcuate member 72 and 74 is enabled to be pivoted about its rivet 78 in a clockwise or counter-clockwise direction. The upper arcuate member 72 is located adjacent the intersection of the upper and rear edges of the lateral side portion while the lower arcuate member 74 is located anterior and inferior to the upper member 72. The opposite end of each of the members 72 and 74 is denoted by the reference numeral 80 and includes an eyelet 82 located thereat. The eyelets 82 in each of the arcuate members are arranged to receive laces to enable the lateral malleoli stabilizing means to be secured to the medial malleoli stabilizing means.

The ankle brace 20 is applied to the foot as follows: The tongue 58 is secured to the jacket by threading a lace 84 (FIG. 5) through the eyelets 60 in the tongue and through the lowermost eyelets 44 in each of the side portions 30 and 32. The foot is then inserted in the jacket so that the elastic strap 50 connecting the underside edges rests under the arch, with the person's heel located within the heel receiving space 48 so that the lateral side portion 30 of the jacket overlies the lateral malleolus and the medial side portion 32 overlies the medial malleolus. The arcuate members 72 and 74 are positioned so that they extend above and below the lateral malleolus on the lateral side of the jacket and above and below the medial mallelus on the medial side of the jacket. The jacket is then laced up the front, via its eyelets 44 and lace 84, in a conventional manner to cause the jacket to tightly encircle the ankle. A second lace 86 is then extended through the eyelets 82 in the bottom arcuate members 74 of the malleoli stabilizing means and crossed over in an X pattern through the eyelets 82 in the top arcuate members 72 thereof. The lace 86 is then tightened and secured. This action causes the upper and lower arcuate members 72 and 74 on the lateral side portion of the jacket to surround and closely conform to the lateral malleolus, while the corresponding arcuate portions 72 and 74 on the medial side portion surround and closely conform to the medial malleolus. Accordingly, the jacket is enabled to tightly conform to the shape of the ankle to localize the application of force thereto.

The conformance to the contours of the ankle joint on either side provide excellent mechanical fixation of the brace to the ankle to support the joint capsule and the ligament attachments. This is of considerable importance when the brace is used on a traumatized ankle, since such conformance facilitates the proprioceptive return of the ankle. In addition, the close mechanical fixation improves stability below the malleoli. This latter characteristic provides control over inversion-eversion motion of the ankle.

Once the malleoli stabilization means are secured as described above, the lift strap 28 is grasped and extended over the instep from the lateral side to the medial side, extended around the back of the jacket to the lateral side and back over the instep to the medial side so that the hook elements 64 engage the loop element 70 to secure the lift strap in place. This action in effect wraps the strap in a figure 8 pattern about the brace to provide lift force to the lateral edge to provide better stabilization of the lateral edge of the foot.

The use of the floating tongue insures that when the brace is in place it fits comfortably and there is no biting or pinching caused by the tongue. In addition, there is no pulling on the ankle brace by the tongue when the brace is in place, which may have the effect of distorting the fit.

The stirrup projecting portions 42 of the side portions 30 and 32 apply additional support to the instep to exert sufficient control thereover, thereby expediting the stabilization of the lateral edge of the foot to preclude its rolling under motion.

The elasticity of the lift strap 28 enables the strap to conform without buckling or without distorting the fit of the jacket when the lift strap is in place.

In the preferred embodiment, as noted heretofore, the jacket is provided with a lining of foam rubber, e.g., neoprene. This feature is of considerable importance since it provides therapeutic benefit to the brace when it is in place by retaining heat within the brace. In addition, the lining provides elasticity for enabling the vinyl side portions, which have limited elasticity, to readily conform to the ankle.

It should be pointed out at this juncture that while the jacket is described as being formed of foam backed vinyl and the malleoli stabilization means being formed of leather, such a construction is not mandatory and the ankle support of the instant invention can thus be formed of any suitable material or combination thereof, such as leather, suede, vinyl, etc. Similarly, while the use of a neoprene liner is preferred, for some applications, such a liner may be omitted or formed of an equivalent material.

Moreover, it must be pointed out at this juncture while only one ankle brace is shown in the drawings herein, the instant invention contemplates the use of a second, or mirror image ankle brace for use on the other foot, if desired.

As will be appreciated from the foregoing, the ankle brace of the instant invention is simple in construction and can be adapted to use on a wide variety of ankles due to the conforming nature of its components. In particular, the malleoli stabilization means enable the ankle brace to conform to the external and internal malleoli which, as is known, are asymmetrically disposed with respect to the ankle. Thus, the brace of the instant invention is a valuable device for preventing damage to a healthy ankle or to provide stability and promote proprioceptive return to an injured ankle.

Without further elaboration, the foregoing will so fully illustrate my invention that others may, by applying current or future knowledge, readily adapt the same for use under various conditions of service.

What is claimed as the invention is:

1. An ankle brace comprising a jacket, malleoli stabilization means and lift strap means, said jacket having a medial side portion and a lateral side portion, each having a bottom, top, front and rear edge and elastic means connecting said portions together at their rear edges and at their bottom edges, said front edges of said side portions being arranged to be secured together by lacing means, said jacket being arranged to fitable about the ankle and contiguous portions of the foot of a person, with the medial side portion of the jacket located over the medial side of the ankle and with the lateral side portion of the jacket located over the lateral side of the ankle, said malleoli stabilizing means comprising lateral stabilizing means secured to the lateral side portion of said jacket for surrounding the external malleolus and medial stabilizing means secured to the medial side portion of said jacket for surrounding the internal malleolus, said lateral and medial stabilzing means being arranged to be releasably secured together by lacing means, said lift strap means being an elongated member having a pair of ends, each arranged for securement to a respective side portion of said jacket, with the intermediate portion of said strap means being wrapped about the instep and the ankle of the person to provide an upward lifting force to the jacket.

2. The brace of claim 1 wherein said jacket includes a thermally insulative lining.

3. The brace of claim 2 wherein said side portions are formed of a flexible material.

4. The brace of claim 3 wherein said lift strap is formed of an elastic material.

5. The brace of claim 4 wherein one end of said lift strap is fixedly secured to the lateral side portion of said jacket and wherein fastening means are provided on the medial side portion of said jacket for releasably securing the other end of said lift strap thereto.

6. The brace of claim 5 wherein said releasable fastening means comprises hook and loop fastening means.

7. The brace of claim 6 wherein said lateral stabilizing means comprise an upper and a lower arcuate member, each member having a pair of ends, one end of each of said members being pivotably secured to the lateral side portion of said jacket and wherein said medial stabilizing means comprise an upper and a lower arcuate member, each secured to the medial side portion of the jacket in the same manner as said lateral stabilizing means.

8. The brace of claim 6 wherein each upper arcuate member is pivotably secured to its associated side portion of the jacket adjacent the top and back edge thereof and wherein each lower arcuate member is pivotably secured to its associated side portion of said jacket anterior and inferior of its associated upper arcuate member.

9. The brace of claim 8 wherein the other end of each of said arcuate members includes means for securement of lacing means thereto.

10. The brace of claim 9 wherein said jacket includes tongue means secured by lacing means to the side portions of said jacket.

11. The brace of claim 10 wherein said arcuate members are formed of a flexible material.

12. The brace of claim 1 wherein said lateral stabilizing means comprise an upper and a lower arcuate member, each member having a pair of ends, one end of each of said members being pivotably secured to the lateral side portion of the jacket and wherein said medial stabilizing means comprise a pair of arcuate members secured to the medial side portion of said jacket in the same manner as said lateral stabilizing means.

13. The brace of claim 12 wherein each upper arcuate member is pivotably secured to its associated side portion of said jacket adjacent the top and back edge thereof and wherein each lower arcuate member is pivotably secured to its associated side portion of said jacket anterior and inferior of its associated upper arcuate member.

14. The brace of claim 13 wherein the other end of each of said arcuate members includes means for securement of lacing means thereto.

15. The brace of claim 14 wherein one end of said lift strap is fixedly secured to the lateral side portion of said jacket and wherein fastening means are provided on said medial side portion for releasably securing the other end of said lift strap thereto.

16. The brace of claim 15 wherein said lift strap is formed of an elastic material.

17. The brace of claim 16 wherein said jacket includes a thermally insulative lining.

18. The brace of claim 17 wherein said jacket includes tongue means secured by lacing means to the side portions of said jacket.

19. The brace of claim 18 wherein said side portions of said jacket are formed of a flexible material.

20. The brace of claim 19 wherein said thermally insulative lining comprises an elastic foam.

* * * * *